US009854356B2

(12) United States Patent
Yamkovoy

(10) Patent No.: US 9,854,356 B2

(45) **Date of Patent: *Dec. 26, 2017**

(54) HEADSET NOISE-BASED PULSED ATTENUATION

(71) Applicant: Bose Corporation, Framingham, MA (US)

(72) Inventor: Paul G. Yamkovoy, Acton, MA (US)

(73) Assignee: Bose Corporation, Framingham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/706,666

(22) Filed: May 7, 2015

(65) Prior Publication Data

US 2015/0245136 A1 Aug. 27, 2015

Related U.S. Application Data

(63) Continuation of application No. 13/409,508, filed on Mar. 1, 2012, now Pat. No. 9,208,773, which is a (Continued)

(51) Int. Cl.
*A61F 11/06* (2006.01)
*H04R 3/00* (2006.01)
(Continued)

(52) U.S. Cl.
CPC ......... *H04R 3/002* (2013.01); *G10K 11/1782* (2013.01); *H04R 1/10* (2013.01);
(Continued)

(58) Field of Classification Search
CPC ........ H04R 3/002; H04R 1/10; H04R 1/1083; H04R 5/033; H04R 1/1041;
(Continued)

(56) References Cited

U.S. PATENT DOCUMENTS 4,764,954 A 8/1988 Tsurusaki et al.
5,369,711 A * 11/1994 Williamson, III ... H03G 3/3026 381/104
(Continued)

FOREIGN PATENT DOCUMENTS

CN 101547389 A 9/2009
CN 201893904 U 7/2011
(Continued)

OTHER PUBLICATIONS

First Japanese Office Action dated Jan. 5, 2016 for Japanese Patent Application No. 2014-559946.
(Continued)

*Primary Examiner* — Akelaw Teshale

(57) ABSTRACT

A headset having a talk-through microphones incorporates an audio circuit that disconnects or compresses a signal representing sounds detected by the talk-through microphones in response to the audio circuit detecting the onset of a peak in the signal that exceeds a predetermined voltage level, and that does so with a rate of change in voltage level that exceeds a predetermined rate of change in voltage level. The duration of the disconnection or compression may be controlled by a timing circuit set to a predetermined period of time that may be retriggerable while amidst the predetermined period of time.

22 Claims, 5 Drawing Sheets

Related U.S. Application Data continuation-in-part of application No. 13/336,207, filed on Dec. 23, 2011, now Pat. No. 9,208,772.

(51) Int. Cl.

| | |
|---|---|
| ***H04R 1/10*** | (2006.01) |
| ***G10K 11/178*** | (2006.01) |
| *H04R 5/033* | (2006.01) |

(52) U.S. Cl.

CPC ......... *H04R 1/1083* (2013.01); *H04R 1/1041* (2013.01); *H04R 5/033* (2013.01); *H04R 2201/107* (2013.01); *H04R 2420/07* (2013.01); *H04R 2460/01* (2013.01)

(58) Field of Classification Search

CPC .......... H04R 2201/107; H04R 2420/07; H04R 2460/01; G10K 11/1782; G10K 11/17

USPC ............................................................ 381/72

See application file for complete search history.

(56) References Cited

U.S. PATENT DOCUMENTS

| | | | | | |
|---|---|---|---|---|---|
| 7,234,340 | B2 * | 6/2007 | Wen | G01H 1/00 | 73/11.04 |
| 7,672,462 | B2 * | 3/2010 | Schneider | H03G 7/002 | 381/102 |
| 8,186,478 | B1 * | 5/2012 | Grason | A61F 11/08 | 181/129 |
| 2003/0118197 | A1 | 6/2003 | Nagayasu et al. | | |
| 2006/0100828 | A1 * | 5/2006 | Lee | G01H 3/08 | 702/190 |
| 2008/0292111 | A1 | 11/2008 | Park | | |
| 2010/0215198 | A1 * | 8/2010 | Ngia | H04R 1/1016 | 381/309 |

FOREIGN PATENT DOCUMENTS

| | | | | |
|---|---|---|---|---|
| EP | 1675429 | A2 | | 6/2006 |
| GB | 2246688 | | * | 2/1992 |
| JP | H01149508 | A | | 6/1989 |
| JP | H06276599 | A | | 9/1994 |
| JP | H11234541 | A | | 8/1999 |
| JP | 2003198719 | A | | 7/2003 |
| JP | 2011097268 | A | | 5/2011 |
| JP | 2011135442 | A | | 7/2011 |

OTHER PUBLICATIONS

First Chinese Office Action dated May 3, 2016 for Chinese Patent Application No. 201280063700.4.

First Chinese Office Action dated Nov. 1, 2016 for Chinese Patent Application No. 201380020101.9.

Second Chinese Office Action dated Dec. 8, 2016 for Chinese Patent Application No. 201280063700.4.

* cited by examiner

HEADSET NOISE-BASED PULSED ATTENUATION

CROSS-REFERENCE TO RELATED APPLICATION

The present application is a continuation of application Ser. No. 13/409,508, filed Mar. 1, 2012, which is a continuation-in-part of application Ser. No. 13/336,207 filed Dec. 23, 2011 by Paul G. Yamkovoy, the disclosure of which is incorporated herein by reference.

TECHNICAL FIELD

This disclosure relates to detecting occurrences of fast-onset environmental noise sounds detected by a talk-through microphone of a headset to momentarily attenuate talk-through audio.

BACKGROUND

With the advent of ever more effective forms of noise reduction headsets to reduce the environmental noise sounds that reach the ears of its user, and possibly impede the user's ability to use one or more features of the headset (e.g., listening to music, engaging in two-way communications, etc.), a growing need has been identified to in some way allow speech sounds of another person in the vicinity of the user to still reach the ears of the user so as to allow the user to carry on a conversation with that other person without removing at least a portion of it from at least one of the user's ears. This has led to the introduction of a "talk-through" (TT) functionality being added to such a headset that employs one or more filtering techniques to separate speech sounds of such another person from other environmental sounds, and to pass those speech sounds through whatever passive noise reduction (PNR) or active noise reduction (ANR) functionality is provided by such a headset, and onward to an ear of its user. Unfortunately, difficulties persist in the provision of both ANR and TT functionality arising from false triggering of audio compressors arising from certain relatively loud environmental sounds having relatively fast onset times (e.g., gun-shot sounds, sounds of explosions, etc.), or electrical noise arising from such events as electrostatic discharges that create pulses that resemble such relatively loud environmental sounds by also having relatively fast onset times.

SUMMARY

A headset having a talk-through microphones incorporates an audio circuit that compresses a signal representing sounds detected by the talk-through microphones in response to the audio circuit detecting the onset of a peak (positive and/or negative) in the signal that exceeds a predetermined voltage level (positive and/or negative voltage level, perhaps a predetermined magnitude of voltage from a zero voltage level), and that does so with a rate of change in voltage level that exceeds a predetermined rate of change in voltage level, the degree of compression possibly being a compression to or near a zero amplitude (perhaps to or near a zero voltage level) and the duration of the compression possibly being controlled by a timing circuit set to a predetermined period of time that may be retriggerable while amidst the predetermined period of time.

In one aspect, a method of controlling sounds acoustically output by an acoustic driver disposed within a casing of an earpiece of a headset includes compressing a signal representing sounds detected by a microphone of the headset that is acoustically coupled to the environment external to the casing in response to detecting an onset of a peak in the signal that exceeds a predetermined voltage level and that has a rate of change in voltage level that exceeds a predetermined rate of change.

In another aspect, a headset includes a first earpiece that includes a first casing and a first acoustic driver disposed therein; a first microphone carried by structure of the communications headset and acoustically coupled to an environment external to the first casing; and an audio circuit coupled to the first acoustic driver and the first microphone, the audio circuit receiving a signal representing sounds detected by the first microphone and providing an output to the first acoustic driver. The audio circuit compresses the signal in response to detecting an onset of a peak in the signal that exceeds a predetermined voltage level and has a rate of change in voltage level that exceeds a predetermined rate of change.

DETAILED DESCRIPTION

What is disclosed and what is claimed herein is intended to be applicable to a wide variety of headsets, i.e., devices structured to be worn on or about a user's head in a manner in which at least one acoustic driver is positioned in the vicinity of an ear; and to a wide variety of communications headsets, i.e., devices additionally structured such that a microphone is positioned towards the user's mouth to enable two-way audio communications. It should be noted that although specific embodiments of headsets incorporating a pair of acoustic drivers (one for each of a user's ears) are presented with some degree of detail, such presentations of specific embodiments are intended to facilitate understanding through examples, and should not be taken as limiting either the scope of disclosure or the scope of claim coverage.

It is intended that what is disclosed and what is claimed herein is applicable to headsets that also provide active noise reduction (ANR), passive noise reduction (PNR), or a combination of both. It is intended that what is disclosed and what is claimed herein is applicable to headsets meant to be coupled to any of a variety of audio devices, including and not limited to, an intercom system (ICS), a radio, or a digital audio player; and via wired and/or wireless connections. It is intended that what is disclosed and what is claimed herein is applicable to headsets having physical configurations structured to be worn in the vicinity of either one or both ears of a user, including and not limited to, over-the-head headsets, behind-the-neck headsets, two-piece headsets incorporating at least one earpiece and a physically separate microphone worn on or about the neck, as well as hats or helmets incorporating earpieces and/or microphone(s). Still other embodiments of headsets to which what is disclosed and what is claimed herein is applicable will be apparent to those skilled in the art.

Figure 1B:
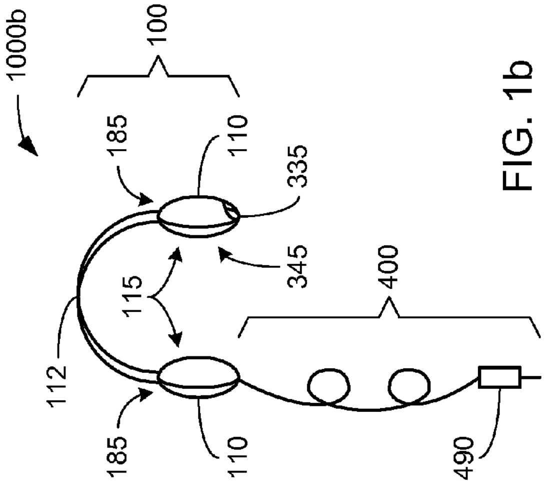
FIGS. 1*a* and 1*b* are each a perspective diagram of a headset.
Figure 1A:
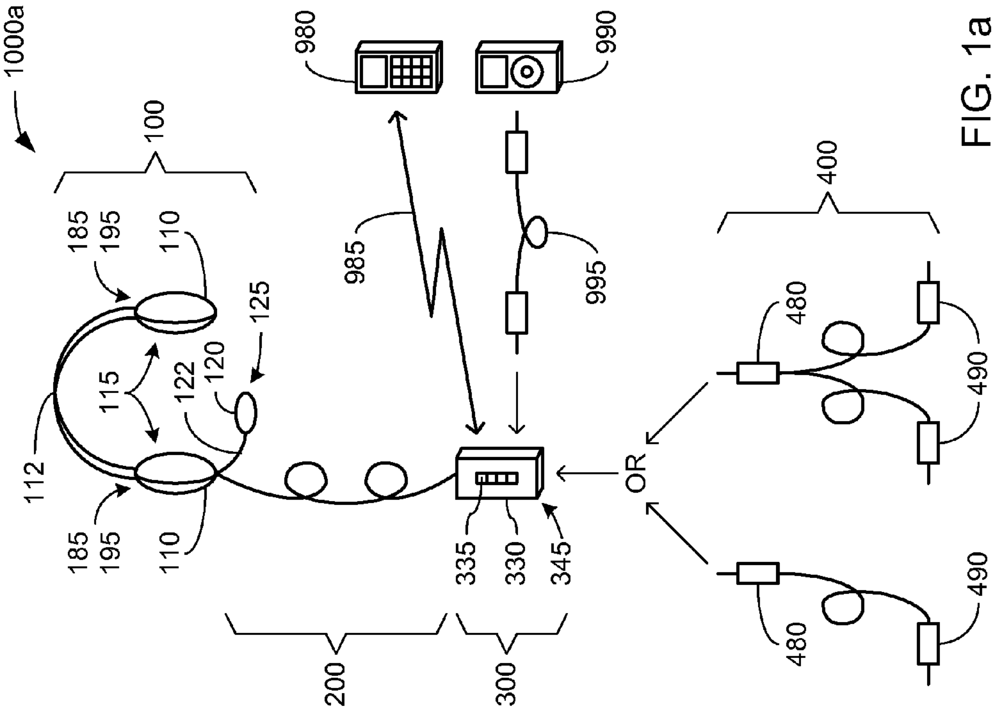

FIGS. 1*a* and 1*b* depict embodiments of headsets 1000*a* and 1000*b* meant to be coupled to an audio device, such as an ICS, radio, tape player, digital audio player, etc. The headset 1000*a* is a communications headset for use in two-way audio communications, and incorporates a head assembly 100, an upper cable 200, a control box 300, and a lower cable 400. The headset 1000*b* is a simpler headset primarily for listening to audio, and incorporates a simpler form of the headset 100 and the lower cable 400.

The head assembly 100 of both headsets 1000*a* and 1000*b* incorporates a pair of earpieces 110 that each incorporate one of a pair of acoustic drivers 115, a headband 112 that couples together the earpieces 110, and a pair of talk-through microphones 185. The head assembly of the headset 1000*a* further incorporates a pair of feedforward ANR microphones 195, a microphone boom 122 extending from one of the earpieces 110, and a microphone casing 120 supported by the microphone boom 122 and incorporating a noise-canceling communications microphone 125. Further incorporated into the casing of at least one of the earpieces 110 and/or of another component of the head assembly 100 is an audio circuit 600 electrically coupled to the acoustic drivers 115 (and/or coupled to the communications microphone 125 in the headset 1000*a*). As depicted, the headsets 1000*a-b* have an "over-the-head" physical configuration. However, despite the depiction of this particular physical configuration, those skilled in the art will readily recognize that the head assembly 100 may take any of a variety of other physical configurations, including physical configurations having only one of the earpieces 110 (and correspondingly, only one of the acoustic drivers 115), physical configurations employing a napeband meant to extend between the earpieces 110 about the back of a user's neck, and/or physical configurations having no band at all. Depending on the size of each of the earpieces 110 relative to the typical size of the pinna of a human ear, each of the earpieces 110 may be either an "on-ear" (also commonly called "supra-aural") or an "around-ear" (also commonly called "circum-aural") form of earcup.

The control box 300 of the headset 1000*a* incorporates a casing 330 that incorporates a control circuit 700. The control box 300 may also incorporate one or more manually-operable controls 335 enabling a user of the headset 1000*a* to manually control aspects of various functions performed by the headset 1000*a*. The control box may further incorporate at least a compartment (not shown) for a battery 345 and/or the battery 345, itself, coupled to the control circuit 700. In contrast, on the headset 1000*b*, the control circuit 700, the controls 335 and/or the battery 345 (if present) are incorporated into one or both of the casings 110.

The upper cable 200 of the headset 1000*a* is made up principally of a multiple-conductor electrical cable extending between and coupling one of the earpieces 110 of the head assembly 100 to the control box 300. In so doing, at least a subset of the conductors of the upper cable 200 couple and convey electrical signals between the audio circuit 600 of the head assembly 100 and the control circuit 700 of the control box 300. In various possible variants of the headset 1000*a*, the upper cable 200 may be formed with a coiled shape as a convenience to users of the headset 1000*a*. Also, the upper cable 200 may additionally incorporate one or more connectors (not shown) on the upper cable 200 where the upper cable 200 is coupled to one of the earpieces 110 and/or where the upper cable 200 is coupled to the casing 330 of the control box 300, thereby making the upper cable 200 detachable from one or both of the head assembly 100 and the control box 300. In contrast, given that both the audio circuit 600 and the audio circuit 700 are incorporated into portions of the head assembly 100 such that the headset 1000*b* does not incorporate the control box 300, the headset 1000*b* also does not incorporate the upper cable 200.

The lower cable 400 is made up principally of another multiple-conductor electrical cable that extends from the control box 300 on the headset 1000*a* or extends from one of the earpieces 100 on the headset 1000*b*. On the headset 1000*a*, the lower cable 400 may be detachable from the control box 300 (via one or more connectors 480) with different variants ending with one or more connectors 490 (two variants being depicted) to enable the headset 1000*a* to be detachably coupled to a wide variety of audio devices. On the headset 1000*b*, a single variant of the lower cable 400 may be more permanently coupled to one of the earpieces 110. At least a subset of the conductors of the lower cable 400 couple and convey electrical signals between the control circuit 700 and circuitry of whatever audio device to which the connector(s) 490 may be coupled. In various possible variants, the lower cable 400 may be formed with a coiled shape as a convenience to users of the headset 1000.

As more specifically depicted in FIG. 1*a*, the headset 1000*a* may be able to be coupled to more than one audio device, perhaps incorporating a wireless transceiver enabling it to be coupled via wireless signals 985 (e.g., infrared signals, radio frequency signals, etc.) to a wireless device 980 (e.g., a cell-phone, an audio playback/recording device, a two-way radio, etc.) to thereby enable a user of the headset 1000*a* to additionally interact with the wireless device 980 through the headset 1000. Alternatively or additionally, the headset 1000*a* may incorporate an auxiliary interface (e.g., some form of connector to at least receive analog or digital signals representing audio) enabling the headset 1000*a* to be coupled through some form of optically or electrically conductive cabling 995 to a wired device 990 (e.g., an audio playback device, an entertainment radio, etc.) to enable a user to at least listen through the headset 1000*a* to audio provided by the wired device 990. Where the control box 300 incorporates the manually-operable controls 335, the manually-operable controls 335 may enable a user of the headset 1000*a* to coordinate the transfer of audio among the headset 1000, the wireless device 980, the wired device 990, and whatever audio device to which the headset 1000*a* may be coupled via the lower cable 400. In contrast, the headset 1000*b* is not specifically depicted as having such capabilities, but alternate variants having such capabilities are certainly possible.

Figure 2A:
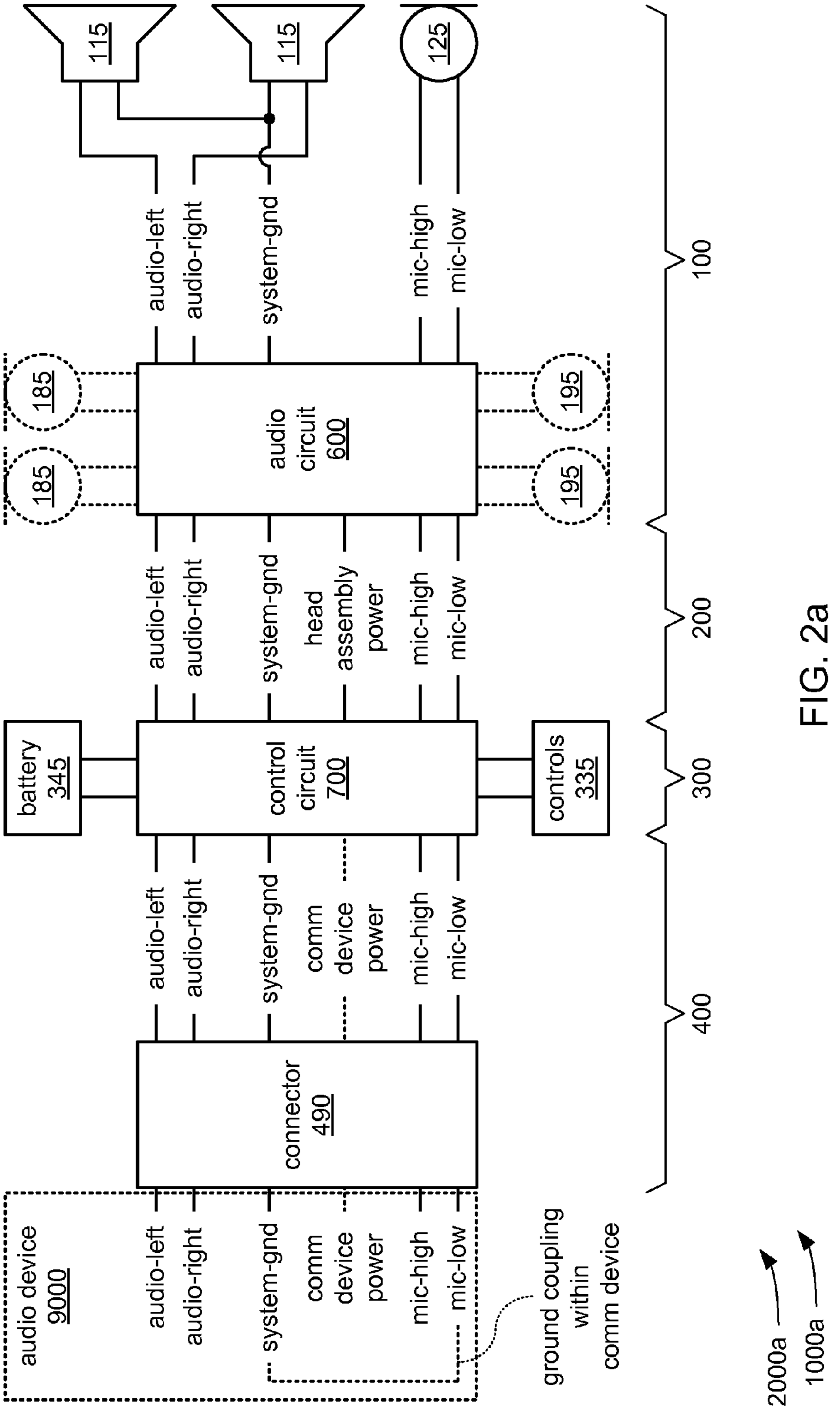
FIGS. 2*a* and 2*b* are block diagrams of portions of a possible electrical architecture of the headset of FIG. 1*a*.

FIG. 2*a* depicts a possible embodiment of an electrical architecture 2000*a* that may be employed by the headset 1000*a*. To facilitate understanding, the headset 1000*a* is depicted as being coupled to an audio device 9000, which in this example, is a communications device enabling two-way audio communications such as an ICS or radio of a vehicle such as an airplane, a military vehicle, etc. Only portions of the audio device 9000 needed to facilitate discussion are depicted. Like FIG. 1*a*, FIG. 2*a* depicts the coupling of the head assembly 100 to the control box 300 via the upper cable 200, and depicts the coupling of the control box 300 to the audio device 9000 via the lower cable 400. FIG. 2*a* further depicts individual conductors of each of the cables 200 and 400.

It should again be noted that the audio circuit 600 may exist entirely within the casing of only one of the earpieces 110; or may be divided into multiple portions, with portions distributed within the casings of each of the earpieces 110 (in variants of the headset 1000 having a pair of the earpieces 110), within the casing 120 that carries the communications microphone 125, and/or elsewhere within the structure of the headset 1000*a*. Thus, although the audio circuit 600 is depicted with a single block for ease of discussion, this should not be taken as an indication that the all of the audio circuit 600 necessarily exists within a single location of the structure of the headset 1000*a*.

As depicted, in the electrical architecture 2000*a*, audio-left and audio-right signals, along with an accompanying common system-gnd serving as a signal return, extend between the audio device 9000 and corresponding ones of the acoustic drivers 115 through conductors within the head assembly 100, conductors of the cables 200 and 400, and portions of the circuits 600 and 700. The provision of the separate audio-left and audio-right signals enables the provision of stereo audio to ears of a user of the headset 1000*a*. As also depicted, mic-high and mic-low signals extend between the audio device 9000 and the communications microphone 125 also through conductors within the head assembly 100, conductors of the cables 200 and 400, and portions of the circuits 600 and 700.

As will be familiar to those skilled in the art, widespread industry practice and/or government regulations in specific industries often dictate that specific forms of audio device supporting two-way audio communications (e.g., the radio or ICS represented by the audio device 9000) provide a microphone bias voltage across the conductors associated with coupling a headset microphone to such forms of audio device to accommodate some types of microphones requiring a bias voltage. As will be familiar to those skilled in the art, it is considered a best practice to maintain the conductors coupling a headset microphone to an ICS or radio (e.g., the depicted conductors mic-low and mic-high) as entirely separate from the conductors coupling a headset acoustic driver to an ICS or radio (e.g., the depicted conductors audio-left, audio-right and system-gnd). As part of such best practice, any coupling of any ground conductor among the conductors associated with that microphone and those associated with that acoustic driver occurs only within the ICS or radio (as depicted with a dotted line within the audio device 9000) in an effort to avoid the creation of a ground loop extending along the length of whatever cabling couples a headset to an ICS or radio.

Further, and with somewhat less consistency even within a given industry, various forms of audio device supporting two-way audio communications may or may not provide a headset with electric power via at least one other conductor coupling that audio device to that headset (e.g., a communications device power conductor, as depicted). Where such power is so provided, it is usually referenced to whatever ground conductor is associated with an acoustic driver of that headset (e.g., the system-gnd conductor), and not one of the conductors associated with a microphone of that headset. As previously depicted and discussed, the lower cable 400 may be detachable from the control box 300 to allow different versions of the lower cable 400 having different versions of the connector(s) 490 to accommodate different forms of a communications device (i.e., different variations of the audio device 9000). As will be familiar to those skilled in the art, the connector(s) with which the audio device 9000 may be provided may or may not support the provision of electric power to a headset, and this may be one of the differences accommodated with different versions of the lower cable 400.

Thus, as depicted, the control circuit 700 is provided with power from one or both of audio device 9000 (via the communications device power conductor of the lower cable 400) and the battery 345. In keeping with other best practices, a ground conductor of the battery 345 is typically also coupled to the system-gnd. In turn, at least one head assembly power conductor of the upper cable 200 then conveys power provided to the control circuit 700 from whatever source to the audio circuit 600. The headset 1000*a* may use that electric power in performing various functions including, and not limited to, amplifying audio for acoustic output by the acoustic driver(s) 115, pre-amplifying audio detected by the communications microphone 125, providing one or more forms of ANR (hence the dotted line depiction of the possible coupling of ANR microphone(s) 195 to the audio circuit 600), powering a wireless transceiver to send and/or receive audio (e.g., a wireless transceiver used to form the communications link 985), performing any of a variety of forms of signal processing on audio acoustically output by the acoustic driver(s) 115 and/or detected by the communications microphone 125, and/or providing a talk-through (TT) function to enable selective passage of speech sounds from the environment external to the casing(s) 110 through whatever passive noise reduction (PNR) and/or ANR that may be provided by the headset 1000*a* so as to reach the ears of a user (hence the dotted line depiction of the possible coupling of talk-through microphone(s) 185 to the audio circuit 600).

As those skilled in the art will readily recognize, government regulations often require a degree of "failsafe" design be employed in headsets supporting two-way audio communications such that basic functionality for carrying out two-way communications (i.e., using a headset with whatever ICS or radio it may be coupled to) not be lost as a result of a loss of power to the headset. Thus, the acoustic driver(s) 115 and the communications microphone 125 must still be operational for two-way communications even if no power is provided by the audio device 9000, the battery 345, or any other source. Thus, it is common practice to provide a mechanism by which signals employed in such basic operation of the acoustic driver(s) 115 and the communications microphone 125 will bypass any amplification or other circuitry (i.e., be conducted among the connector(s) 490, the acoustic driver(s) 115 and communications microphone 125 without interruption) when such power loss occurs.

With the manually-operable controls 335 carried by the control box 300, and coupled to the control circuit 700 that is also at least partly located within the control box 300, provision is made in the headset 1000*a* for signals to control audio functions performed by the audio circuit 600 to be conveyed via the upper cable 200 from the control box 300 to the head assembly 100. What the audio circuit 600 is signaled to do in performing one or more functions may be determined by a user through their operation of the manually-operable controls 335 and/or may be determined in a more automated manner in response to available electric power. In one possible approach, electric power is conveyed by at least one head assembly power conductor of the upper cable 400 to the audio circuit 600 with a selectively variable voltage level as a mechanism to control one or more aspects of the performance of one or more of these various functions. In this way control signals may be conveyed from the control circuit 700 to the audio circuit 600 without use of distinct control conductors added to the upper cable 400 and without use of a digital serial signaling system that could add undesirably complex encoder and decoder circuitry to the control circuit 700 and the audio circuit 600. Avoiding the addition of distinct control signal conductors and digital serial signaling reduces avenues for the introduction of electromagnetic interference (EMI) by reducing the quantity of conductors that may tend to act as antennae for receiving EMI, by avoiding the occurrence numerous transitions in voltage level and/or direction in current flow that accompanies the use of digital serial signals. Further, employing power conductors in dual roles of conveying power and conveying control signals also reduces avenues for the introduction of EMI due to their inherent tendency to act as AC-coupled shorts to ground.

Figure 2B:
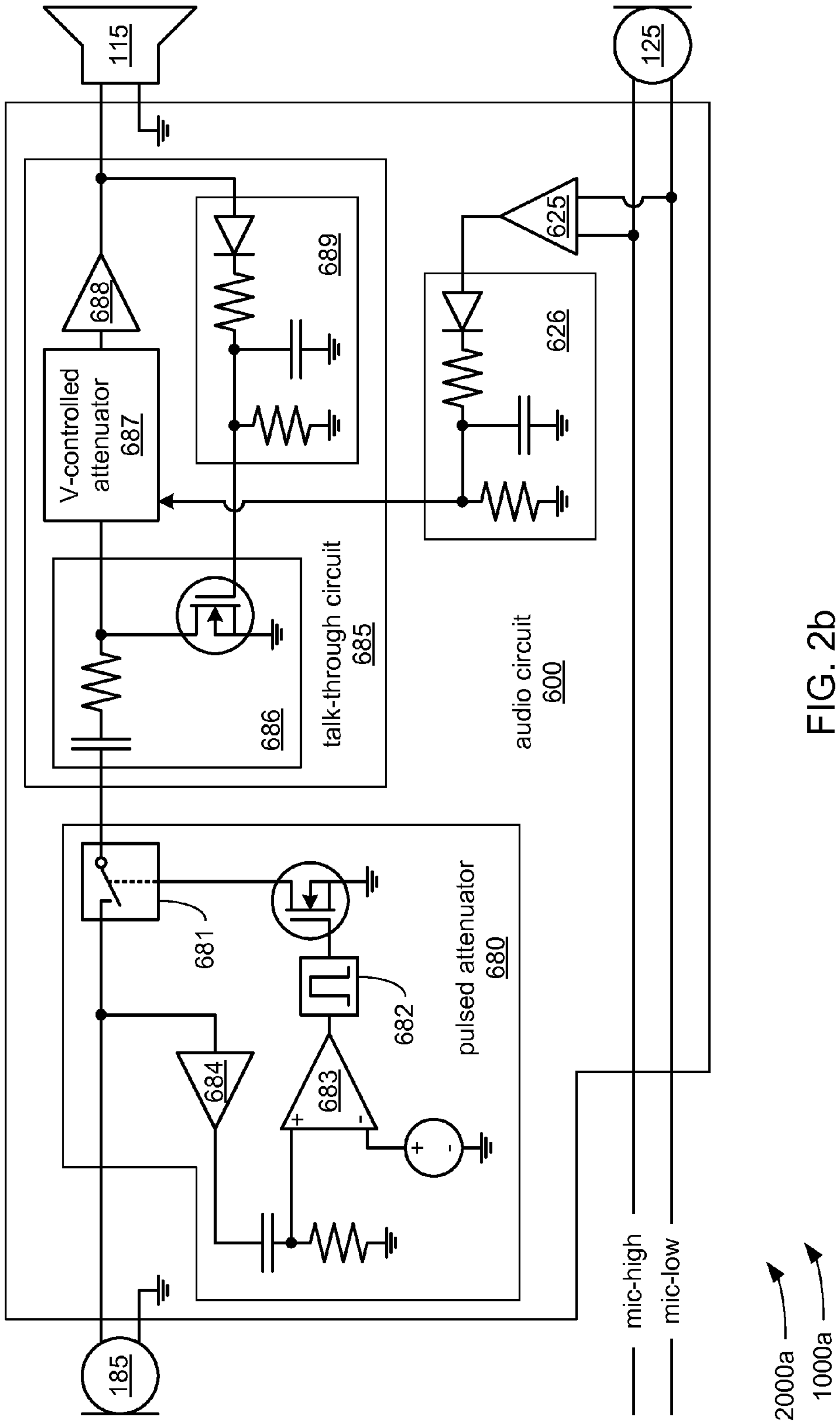

FIG. 2*b* depicts portions of a possible implementation of the audio circuit 600 within the electrical architecture 2000*a* of FIG. 2*a* germane to implementing talk-through functionality in greater detail. Thus, portions more germane to other features of the architecture 2000*a* have been omitted for sake of clarity. Also for sake of clarity, components of the audio circuit 600 associated with only one of the earpieces 110, and not a pair of the earpieces 110, are depicted. Thus, although what is depicted could be part of a form of the headset 1000*a* that incorporates a pair of the earpieces 110 (and therefore, at least a pair of the acoustic drivers 115, as well as duplicate sets of associated components within the audio circuit 600), only one of the acoustic drivers 115 and its associated components within the audio circuit 600 are depicted to avoid unnecessary visual clutter.

As depicted, the audio circuit 600 in this variant of the electrical architecture 2000*a* incorporates a talk-through circuit 685 coupled to the acoustic driver 115, a pulsed attenuator 680 coupled to the talk-through microphone 185 and to the talk-through circuit 685, a differential amplifier 625 to tap electrical signals representing audio detected by the communications microphone 125 at its inputs, and an envelope detector 626 coupled to both the output of the differential amplifier 625 and to the talk-through circuit 685. In turn, the talk-through circuit 685 is depicted as incorporating a controllable attenuator 686 coupled to and receiving the output of the pulsed attenuator 680, a voltage-controlled attenuator 687 coupled to the output of the controllable attenuator 686, an audio amplifier 688 coupled by its input to the output of the voltage-controlled attenuator 687 and by its output to the acoustic driver 115, and an envelope detector 689 also coupled to the output of the audio amplifier 688 and coupled to a control input of the controllable attenuator 686. The pulsed attenuator 680 is depicted as incorporating a microphone amplifier 684 coupled by its input to the talk-through microphone 185, a comparator 683 coupled by its inputs to the output of the microphone amplifier 684 through a high-pass filter (formed by a capacitor and a resistor) and to a reference voltage source, a retriggerable monostable multivibrator 682 coupled by its input to the output of the comparator 683 and coupled by its output to the gate of a MOSFET, and an analog switch 681 coupled by a control input to the MOSFET and through which the controllable attenuator 686 is selectively coupled to the talk-through microphone 185 under the control of the MOSFET.

Again, it should be noted that only a single acoustic driver 115 and its associated circuitry within the audio circuit 600 (e.g., the talk-through circuit 685 and the pulsed attenuator 680) are depicted for sake of visual clarity. Thus, in embodiments of the headset 1000*a* having a pair of the earpieces 110, there would be a pair of the acoustic drivers 115, each having an associated one of a pair of the talk-through circuits 685 coupled to it, and the single envelope detector 626 would be coupled to each of those talk-through circuits 685. Further, each one of the pair of the talk-through circuits 685 may have an associated one of a pair of the talk-through microphones 185 coupled to it through an associated one of a pair of the pulsed attenuators 680. Alternatively, a single pulsed attenuator 680 associated with a single talk-through microphone 185 may be coupled to both talk-through circuits 685 of a pair of talk-through circuits 685.

It should be noted that unlike the communications microphone 125, the talk-through microphone 185 is not a noise-canceling microphone, and this reflects differences in the functions performed by each. It is advantageous and preferred that the communications microphone 125 be a noise-canceling type of microphone such that it is a near-field microphone that detects the speech sounds emanating from the mouth of a user of the headset 1000*a* in the near-field, while tending to ignore far-field sounds. In contrast, it is advantageous and preferred that the talk-through microphone 185 not be such a noise-canceling type of microphone such that it is able to detect far-field sounds (e.g., speech sounds emanating from someone other than the user), as well as near-field sounds.

As those familiar with talk-through functionality will readily recognize, the talk-through circuit 685 operates to convey speech sounds emanating from persons other than a user of the headset 1000*a*, as detected by at least one talk-through microphone 185 (carried by a portion of the headset 1000*a* in a manner that acoustically couples it to the external environment, and to which the talk-through circuit 685 is indirectly coupled through the pulsed attenuator 680), to the acoustic driver 115 to allow the user to hear those speech sounds despite whatever PNR and/or ANR is provided by the headset 1000*a*, which would otherwise normally prevent those speech sounds from being heard by the user. To avoid conveying sounds other than speech sounds through such PNR and/or ANR, the talk-through circuit 685 conveys only sounds detected by the talk-through microphone 185 that are within a predetermined range of audio frequencies associated with human speech. Although variants of the talk-through circuit 685 are possible that incorporate a distinct bandpass filter (not shown) that would separate sounds within such a range to be conveyed from sounds outside such a range (such that they are not to be conveyed), variants of the talk-through circuit 685 are possible that employ a band-limited variant of the audio amplifier 688 such that the audio amplifier 688 performs this bandpass filtering function in addition to amplification.

Within the talk-through circuit 685, the envelope detector 689 and the controllable attenuator 686 cooperate to form one possible implementation of an audio compressor that monitors the amplitude of the output of the audio amplifier 688, and that acts to reduce the amplitude of the audio signal received by the audio amplifier 688 from the talk-through microphone 185 in response to detecting instances of the amplitude of the output of the audio amplifier 688 provided to the acoustic driver 115 exceeding a predetermined threshold. Thus, this compressor created through this cooperation is a closed-loop compressor. It should be noted that alternate implementations of the talk-through circuit 685 are possible in which this audio compressor is not present and with the input of the audio amplifier 688 being more directly coupled to the talk-through microphone 185 (i.e., perhaps with only the voltage-controlled attenuator 687 and/or the pulsed attenuator 680 between them), and it should be noted that alternate implementations of the talk-through circuit 685 are possible in which such compression is provided by a compressor implemented in an entirely different manner (e.g., an open-loop compressor). However, it is seen as desirable to provide such audio compression functionality (in whatever way in which it may be implemented) in the talk-through circuit 685 as a safety feature to protect the hearing of a user of the headset 1000*a* by preventing excessively loud environmental sounds from being conveyed by the talk-through circuit 685 to an ear of the user.

The controllable attenuator 686 is formed from a combination of a capacitor, a resistor and a MOSFET coupled in a manner providing both AC coupling to the talk-through microphone 185 (through the analog switch 681 of the pulsed attenuator 680) and a variable voltage divider that will be readily familiar to those skilled in the art of audio compression. The gate input of the MOSFET of the controllable attenuator 686 is coupled to the output of the envelope detector 689 to enable the envelope detector 689 to operate that MOSFET to control the attenuation to which that MOSFET subjects the signal from the talk-through microphone 185.

The envelope detector 689 is formed from a combination of a diode, resistors and a capacitor coupled in a manner that will also be readily familiar to those skilled in the art of audio compression. The anode of the diode is coupled to the output of the audio amplifier 688, and its cathode is coupled to a first one of the resistors. In turn, the first one of the resistors is further coupled to the capacitor and the second one of the resistors (both of which are further coupled to ground), as well as to the gate input of the MOSFET of the controllable attenuator 686. The diode enables current to flow from the output of the audio amplifier 688 in a manner that charges the capacitor through the first resistor (with the first resistor controlling the rate of charging), but does not allow that charge to be subsequently drained by the output of the audio amplifier 688. Instead, it is the second resistor that provides a controlled rate of drain of that charge—the gate input of the MOSFET of the controllable attenuator 686 having too high an impedance to ground to provide another path of current flow by which the capacitor may be drained. Thus, the envelope detector, effectively acts as an integrator of peaks in the audio signal output by the audio amplifier 688, with the capacitor storing a charge built up by the higher amplitudes of the output of that signal, and discharging at a controlled rate through the second resistor, with the resulting voltage level to which the capacitor has been charged being presented to the gate input of the MOSFET.

Figure 3:
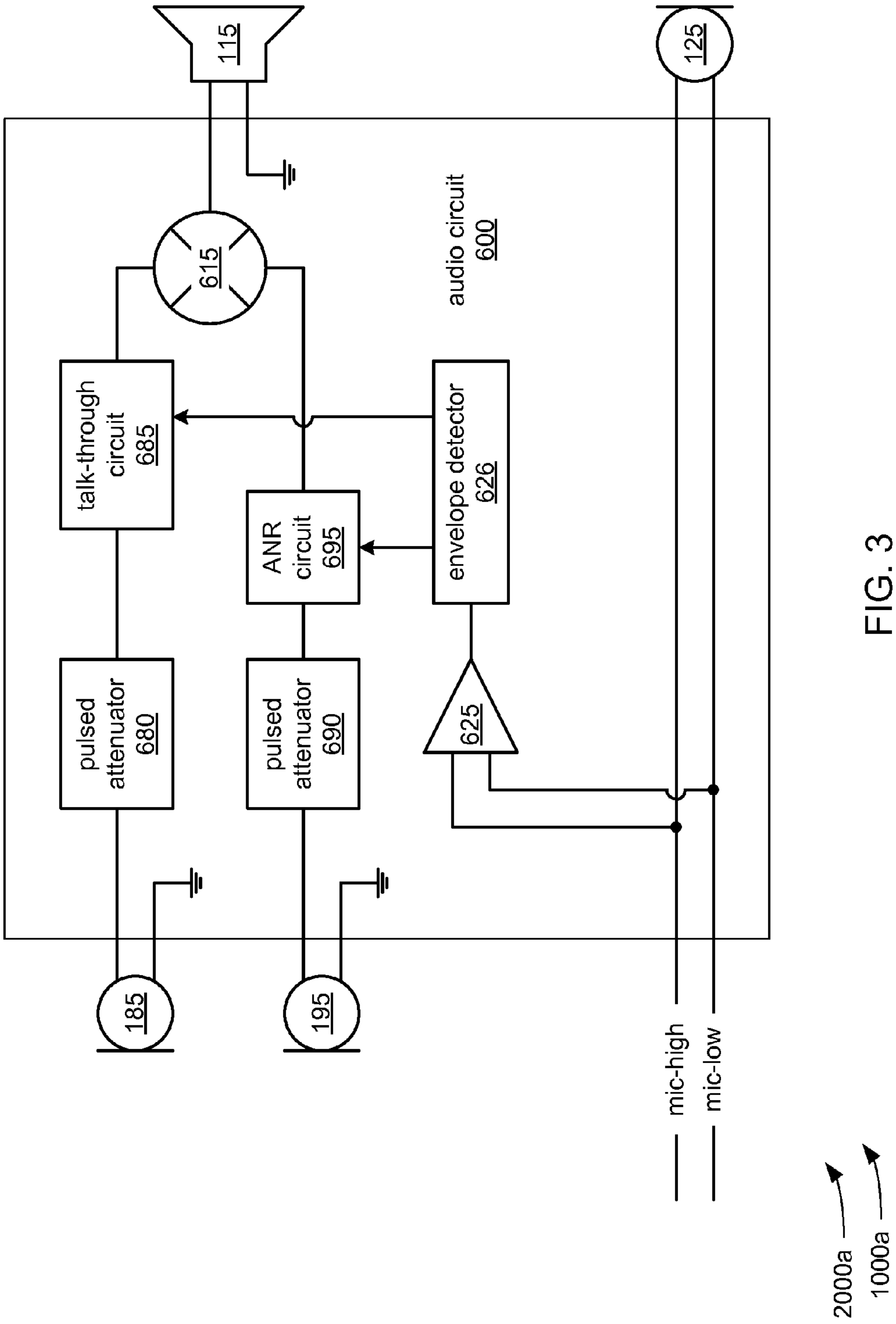
FIG. 3 is a block diagram of portions of a variant of the electrical architecture of FIGS. 2*a* and 2*b* incorporating ANR.

It should be noted that the depiction of the envelope detector 689 in FIG. 3 may be more symbolic of its theory of operation than schematic, as various component substitutions may be made as those skilled in the art will readily recognize. For example, the depicted passive diode may be replaced with an active circuit having a behavior that more closely befits an ideal diode in which the forward bias voltage drop is (or is quite close to) zero. It should also be noted that since the diode and the first resistor are coupled in series to convey the output of the audio amplifier 688 therethrough, the order in which they are depicted as being coupled may be reversed. It should further be noted that, as depicted, the envelope detector 689 is a variant of half-wave envelope detector that detects only positive peaks (while ignoring negative peaks), and that as an alternative, full-wave variants are possible that detect both positive and negative peaks. In other words, to put it more broadly, the envelope detector 689 may be implemented in any of a variety of ways other than what is depicted.

By interposing the envelope detector 689 between the output of the audio amplifier 688 and the gate input of the MOSFET of the controllable attenuator 686 (as opposed to more directly coupling the output of the audio amplifier 688 to that gate input), the controllable attenuator 686 is prevented from being caused to provide and cease to provide attenuation of the signal from the talk-through microphone with each positive peak that occurs in the output of the audio amplifier 688. Instead, the controllable attenuator 686 is caused to provide attenuation in a more continuous manner throughout periods of time in which multiple peaks exceeding the predetermined threshold level of amplitude for the output of the audio amplifier 688 occur, and to cease providing attenuation only after such periods have passed (the threshold being set, at least partially, by the threshold voltage of the gate of the MOSFET of the controllable attenuator and the voltage drop of the forward bias voltage across the diode of the envelope detector 689 in the particular implementation of the envelope detector 689 that is shown). In causing the controllable attenuator 686 to behave in this manner, the time delay by which the envelope detector 689 responds to the occurrence of a peak (either an isolated peak or the first of multiple adjacent peaks) exceeding the predetermined threshold (also known as the “attack time”) is necessarily set by the resistance of the first resistor and the capacitance of the capacitor, as those skilled in RC circuits will readily recognize. Further, the time required for the capacitor to drain sufficiently that the MOSFET is no long provided with a voltage triggering attenuation (also known as the “decay time”) is necessarily set by the capacitance of the capacitor and the resistance of the second resistor. Thus, the choice of the capacitance of the capacitor and the resistances of the first and second resistors determine the behavior of the compressor function brought about by the cooperation of the envelope detector 689 and the controllable attenuator 686.

The envelope detector 626 is formed from a combination of a diode, resistors and a capacitor coupled in a manner that is substantially similar to what has just been described of the envelope detector 689 (but, just as in the case of the envelope detector 689, the envelope detector 626 may be implemented in any of a variety ways, including as an active circuit). However, instead of being employed to integrate peaks in the signal output by the audio amplifier 688, the envelope detector 626 is employed to integrate peaks in the signal output by the communications microphone 125, as received by the envelope detector 626 through the differential amplifier 625. As previously discussed, it is considered a best practice to effect any coupling of one of the mic-low or mic-high conductors to ground only at the location of whatever communications-type audio device to which the headset 1000*a* is coupled through the connector(s) 490 (e.g., the audio device 9000). Thus, coupling the positive and negative inputs of the differential amplifier 625 to the mic-low and mic-high conductors enables whatever signal carried by them to be tapped without causing either of them to be coupled to ground at the location of the audio circuit 600 (taking advantage of the very high impedance of typical differential amplifiers). Still, as those skilled in the art will readily recognize, it is not inconceivable to use a single-ended variant of amplifier in place of the differential amplifier 625, perhaps along with coupling the mic-low signal to ground within the audio circuit 600 while coupling the mic-high signal to the single-ended input of such an amplifier.

The output of the integration performed by the envelope detector 626 is coupled to a gain input of the voltage-controlled attenuator 687, thereby allowing a signal representing an integration of peaks in signals representing audio detected by the communications microphone 125 to be employed to selectively reduce the gain of the signal representing sounds detected by the talk-through microphone

185 that is provided to the input of the audio amplifier 688. It should be noted that although the use of an attenuator that is a separate and distinct component from the audio amplifier 688 to serve as the mechanism by which gain may be reduced under the control of the envelope detector 626 is depicted, other embodiments are possible in which the gain of the audio amplifier 688 is controllable and the envelope detector 626 is more directly coupled to the audio amplifier 688 (i.e., coupled in some manner to a gain control input of the audio amplifier 688) to employ the audio amplifier 688 to reduce gain. This depiction of a separate and distinct component to actually effect a reduction in gain has been done partially to make clear that it is a reduction in gain that is meant to be carried out under the control of the envelope detector 626, and not an increase.

In this way, a linkage between differential signal activity occurring across the mic-low and mic-high conductors and a reduction of the gain of talk-through audio is formed such that when a user of the headset 1000*a* speaks, the gain of the signal representing sounds detected by the talk-through microphone 185 is reduced for a period of time that starts with an attack time and ends with a decay time that are at least partially controlled by the capacitance of the capacitor and the resistances of the resistors of the envelope detector 626. Thus, an open-loop compressor is formed by the interaction between the envelope detector 626 and the voltage-controlled attenuator 687 to implement this linkage. This addresses the problem of a user of the headset 1000*a* hearing his own voice to a greater than normal degree through the talk-through functionality of the headset 1000*a* whenever the user speaks. As those familiar with the physiology and acoustics of human speech will readily recognize, it is normal for a person to hear their own speech sounds when they speak, partially as a result of vocal sounds being internally conveyed to their ears through the Eustachian tubes, bone conduction and conduction through other structures within the neck and head; and partially as a result of vocal sounds being carried in the air from the vicinity of their mouth to the vicinities of both of their ears (presuming that the entrances to their ear canals are not covered). However, although a user hearing themselves talk to such a degree is normal, it is very possible that the talk-through functionality of the headset 1000*a* may cause a user's own voice to be conveyed to their ears with an unnaturally high amplitude and/or altered in some other way that may be unpleasant and/or distracting, and which may mask other sounds that they desire to hear (e.g., another person's voice).

Further, depending on the placement of the talk-through microphone 185 relative to the vicinity of a user's mouth and/or how loudly they speak, it is possible that their own speech sounds may be detected by the talk-through microphone 185 as being sufficiently loud that amplification at a normal gain level by the audio amplifier 688 causes triggering of the compression function provided by the combination of the envelope detector 689 and the controllable attenuator 686. Thus, instead of there being a problem of a user hearing their own voice to a degree that is unnaturally loud and/or in a manner that is unnatural in other ways through the talk-through functionality (as described above), there may be a problem of a user experiencing a momentary loss of talk-through functionality that lasts both while they are speaking and for the duration of the decay time of that compression function following the instant they cease speaking. Depending on the length of that decay time, this could actually impede a user having a conversation with someone else by causing the user to become unable to hear what the other person is saying whenever the user speaks and for some additional period of time (i.e., that decay time) after the user stops talking. In effect, for example, a user of the headset 1000*a* may ask someone else a question, but be unable to hear either themselves asking the question or at least the start of the other person's answer. By reducing the gain with which the signal representing sounds detected by the talk-through microphone 185 is provided to the audio amplifier 688 whenever the user speaks, talk-through functionality is maintained, but at a reduced gain level that both prevents the user from hearing their own voice at an unnaturally loud level and that also precludes the output of the audio amplifier 688 reaching an amplitude that triggers compression.

In order for the addition of the open-loop compressor formed by the combination of the envelope detector 626 and the voltage-controlled attenuator 687 to effectively prevent unwanted triggering of the closed-loop compressor formed by the combination of the envelope detector 689 and the controllable attenuator 686, at least the attack time of the open-loop compressor formed by the combination of the envelop detector 626 and the voltage-controlled attenuator 687 must be shorter than the attack time of the closed-loop compressor formed by the combination of the envelop detector 689 and the controllable attenuator 686. However, it is preferred that this open-loop compressor operate generally faster than this closed-loop compressor, and therefore, it is preferable that the decay time of this open-loop compressor is also shorter than the decay time of this closed-loop compressor.

Within the pulsed attenuator 680, the input of the microphone amplifier 684 is coupled to the talk-through microphone 185 to tap signals from the talk-through microphone 185 representing sounds that it has detected as those signals are selectively conveyed to the controllable attenuator 686 through the analog switch 681. As depicted, the input of the microphone amplifier 684 is not AC-coupled to the talk-through microphone 185 (as the input of the audio amplifier 688 is) through a capacitor, but other embodiments are possible in which it could be. The output of the microphone amplifier 684 is coupled to a capacitor that is further coupled both to a first input of the comparator 683 and to a resistor, with the resistor being further coupled to ground. The capacitor and resistor cooperate to form a high-pass filter to pass through only signals from the output of the microphone amplifier 684 that represent higher frequency sounds (i.e., sounds having a frequency greater than a specific predetermined frequency) to that first input of the comparator 683. The second input of the comparator 683 is coupled to a voltage source that is further coupled to ground. The voltage source provides the comparator a reference voltage level against which to compare the voltage levels of signals provided to the comparator 683 by that high-pass filter. The output of the comparator 683 is coupled to the input of the retriggerable monostable multivibrator 682, the output of which is coupled to the gate input of a MOSFET of the pulsed attenuator 680. The MOSFET is further coupled to ground and to the control input of the analog switch 681 to selectively ground this control input of the analog switch 681 under the control of the output of the retriggerable monostable multivibrator 682. Grounding of this control input of the analog switch 681 through the MOSFET causes opening of the analog switch 681, thereby breaking the coupling of the signal output of the talk-through microphone 185 to the controllable attenuator 686 through the analog switch 681.

The microphone amplifier 684, the comparator 683, the retriggerable monostable multivibrator 682 and still other components cooperate to monitor signals output by the talk-through microphone 185 and to control the analog switch 681 to selectively couple the talk-through microphone 185 to the input of the controllable attenuator 686 of the talk-through circuit 680. Thus, the pulsed attenuator 680 is yet another circuit that acts on the audio signal received by the audio amplifier 688 from the talk-through microphone 185. Somewhat like the compressor formed by the cooperation of the envelope detector 689 and the controllable attenuator 686, the pulsed attenuator 680 monitors talk-through audio and acts in response to particular conditions detected in the signal representing the talk-through audio. However, the pulsed attenuator 680 acts more quickly than that compressor and in response to different conditions. Through use of the envelope detector 689 having attack and decay times chosen to integrate peaks in audio so as to avoid providing compression in response to each individual peak, that closed-loop compressor is caused to compress only talk-through audio having too high an amplitude of multiple peaks in duration, and therefore, is unable to respond quickly enough to specific characteristics of a single peak (positive and/or negative) of sound detected by the talk-through microphone 185 to avoid allowing that single peak to be amplified by the audio amplifier 688 and passed on in its entirety to an ear of a user of the headset 1000*a*.

The pulsed attenuator 680 addresses this insufficiency through the use of the high-pass filter formed by the resistor and the capacitor that are coupled to the first input of the comparator 683 to act as a differentiator with resistance and capacitance values selected to enable detection of the onset of a single peak in which the onset has a relatively fast rate of change in voltage level that exceeds a predetermined rate. Additionally, the comparator 683 detects when the voltage level of such an onset has also exceeded a predetermined voltage level. In particular, this depicted version of a differentiator combined with a comparator in the manner depicted forms a differentiator and comparator combination that detects the onset of positive peaks (not negative peaks) with a relatively fast rise time (not a relatively fast rate of negative-going change in voltage level). In this use of this differentiation and comparison, a presumption is made that a peak having an onset that has both a relatively fast rise time that exceeds the predetermined rise time and a voltage level that exceeds the predetermined voltage level will be a peak that will ultimately reach an amplitude (i.e., a voltage level) that is undesirably high. In other words, while the envelope detector 689 integrates peaks to enable detection and compression of a longer period event of higher amplitude than is desirable (thus requiring multiple peaks of undesirably high amplitude to have occurred before detection occurs), this combination of differentiator and comparator detects the onset of what appears likely to be a peak that will reach an undesirably high amplitude to enable action to be taken before it actually does so. In essence, the pulsed attenuator 680 attempts to predict such a peak to enable a preemptive response.

Again, it should be pointed out that other variants of differentiator and comparator circuits are possible that, either in lieu of or in addition to detecting the onsets of such positive peaks, would detect the onset of a negative peak having a relatively fast rate of negative-going change in voltage level and where the voltage level exceeds the magnitude of a predetermined negative voltage level. Thus, this illustration of this depicted variant of pulsed attenuator 680 should be seen as only one example implementation, and it may be deemed more desirable in some situations to implement a form of the pulsed attenuator 680 that responds to the onset of either positive or negative peaks of undesirably high amplitude (i.e., peaks ultimately achieving undesirably high magnitudes of voltage levels that are either positive or negative voltage levels) by detecting a high rate of change in voltage level that exceeds a predetermined rate of change without regard to whether it is a negative-going or positive-going rate of change and by detecting the exceeding of a predetermined level of voltage relative to a reference ground level without regard to whether it is a positive or negative voltage level.

In the implementation of the pulsed attenuator 680 that is depicted, the response to detecting what appears to be the onset of such a (positive) peak is a momentary disconnection (effectively momentary compression down to a zero or near-zero amplitude) of the signal output by the talk-through microphone 185 from the controllable attenuator 686 (and thus, ultimately a momentary disconnection of the talk-through microphone 185 from the input of the audio amplifier 688) to prevent such a predicted (positive) peak from ever being conveyed to the audio amplifier 688 such that it can never be passed on to an ear of a user of the headset 1000*a*. However, it should be noted that other implementations of the pulsed attenuator 680 are possible in which the response is momentary compression to a lesser extent such that the predicted (positive) peak is able to be heard at an amplitude within a predetermined limit, rather than momentary disconnection (i.e., momentary compression down to a zero or near-zero amplitude).

However the pulsed attenuator 680 is actually implemented (e.g., whether it detects the onset of only one or both positive and negative peaks), whatever components are used in implementing the pulsed attenuator 680 are preferably chosen to be quick enough in their operation that the analog switch 681 (or its equivalent in other implementations) will be operated quickly enough to prevent a predicted peak from being conveyed through to the input of the audio amplifier 688. Thus, it is preferred that the pulsed attenuator 680 have what might be called an "attack time" that is relatively fast, especially in comparison to the attack time of the compressor formed by the cooperation of the envelope detector 689 and the controllable attenuator 686. The duration of the momentary disconnection (or compression to a lesser degree in other possible implementations) is determined by the period of time to which the retriggerable monostable multivibrator 682 (or its equivalent in other implementations) is set to drive the gate of the MOSFET with a signal that will cause the MOSFET to operate the analog switch 681 to be open to break the coupling of the talk-through microphone 185 to the controllable attenuator 686. The retriggerable monostable multivibrator 682 is preferably set to a predetermined period of time selected to closely match the expected duration of at least one variety of the peaks that are expected to arise from sounds expected to be detected by the talk-through microphone 185 and that are desired to be blocked. It is desired that the pulsed attenuator 680 act to block little more than an individual one of such peaks from reaching the audio amplifier 688 to minimize the disruption in conveying other talk-through audio sounds from the talk-through microphone 185 to the audio amplifier 688. Thus, it is also preferred that the pulsed attenuator 680 act with what might be called a "decay time" that is also relatively fast, again especially in comparison to the decay time of the compressor formed by the cooperation of the envelope detector 689 and the controllable attenuator 686. Ultimately, the intention is that a user of the headset 1000*a* is able to listen to another person through the talk-through microphone 185, and experience only the briefest interruption in hearing the other person that is necessary to prevent a sound having a peak of undesirably high amplitude from being conveyed to an ear of the user via the audio amplifier 688 and the acoustic driver 115.

Indeed, similarly to the envelope detector 626 being previously discussed as preferably having attack and decay times that are faster than those of the envelope detector 689 so as to act to prevent a user's own voice sounds from possibly triggering compression (by the cooperation of the envelope detector 689 with the controllable attenuator 686), it is preferred that the attack and decay times of the pulsed attenuator 680 also be fast enough to similarly prevent triggering of compression by a sound detected by the talk-through microphone 185 having little more than a single peak of undesirably high amplitude (i.e., a peak predicted to reach an undesirably high positive and/or negative magnitude). In other words, just as it is desired that such a peak of such a sound never reach the audio amplifier 688 so as to avoid it being amplified and passed on to an ear of a user, it is also desired that such a peak of such a sound never reach the audio amplifier 688 so as to avoid having an amplified form of that peak reach the envelope detector 689 and charge the capacitor therein sufficiently to trigger compression. Without incorporating the pulsed attenuator 680, the possibility exists that a sound having a single peak of undesirably high amplitude may be detected by the talk-through microphone, then amplified by the audio amplifier 688 and then acoustically output by the acoustic driver 115 to a user's ear before the compressor formed by the cooperation of the envelope detector 689 and the controllable attenuator 686 can respond, but be of high enough amplitude that the capacitor of the envelope detector 689 is charged sufficiently by the single pulse to trigger compression such that the user is deprived of talk-through functionality for the period of time dictated by the attack and decay times of the envelope detector 689—a result that would provide the user with no protection from that peak in the talk-through sound and additionally render the user incapable of hearing what others nearby are saying for a brief time after that peak.

One specific application of the headset 1000*a* that is contemplated is by infantry personnel in a battlefield setting where gunshot and explosion sounds are expected. Of particular concern is when an infantryman using the headset 1000*a* fires his own gun. While the communications microphone 125, being a noise-canceling microphone as previously discussed, will tend to reject the sound of the gunshot from that user's own gun, the talk-through microphone 185 will not do so. Analysis of typical gunshot sounds reveals that they are made up of an initial peak of very high amplitude followed by subsequent peaks of greatly diminished amplitude (i.e., there is a high rate of decay in amplitude following that initial peak) such that it is the initial high amplitude peak that poses the greatest concern. The compressor formed by the cooperation of the envelope detector 689 and the controllable attenuator 686 will respond sufficiently slowly that such a peak will be allowed to be conveyed from the talk-through microphone 185 through the audio amplifier 688 and to the acoustic driver 115 before compression can take place, and yet, such a peak will likely be of high enough amplitude to actually trigger compression of subsequent sounds (including sounds unrelated to the gun shot) for some period of time after such a peak.

However, with the pulsed attenuator 680 in place, the onset of that initial peak is received by the microphone amplifier 684 from the talk-through microphone 185, and is amplified before being provided to the high-pass filter formed by the resistor and capacitor, and subsequently being provided to the comparator 683. Presuming that the onset of that initial peak has a rate of change that exceeds the predetermined rate of change in voltage level, the high-pass filter allows the now-amplified onset of that initial peak to be conveyed to the first input of the comparator 683, where it is compared to the predetermined voltage level as set by the reference voltage level provided at the second input of the comparator 683 by the reference voltage source. Presuming that the now-amplified onset of that initial peak exceeds the predetermined voltage level, the comparator 683 triggers the retriggerable monostable multivibrator 682, causing it to drive the gate input of the MOSFET such that the MOSFET couples the control input of the analog switch 681 to ground for the predetermined period of time to which the retriggerable monostable multivibrator 682 has been set, thereby breaking the coupling of the talk-through microphone 185 ultimately to the input of the audio amplifier 688 for a period of time sufficient to prevent that initial peak from reaching the audio amplifier 688.

As its name suggests, the retriggerable monostable multivibrator 682 is able to be "retriggered" such that the time period for which it is set to cause the analog switch 681 to open (through driving the MOSFET, as has been described) can be restarted in response to the detection of the onset of another peak that has the aforedescribed requisite characteristics before a currently occurring one of such time periods is over. Thus, if there is an instance of a first peak having the aforedescribed characteristics (e.g., an initial peak of a first gunshot sound) followed quickly enough by an instance of a second peak also having the aforedescribed characteristics (e.g., an initial peak of a second gunshot sound) such that the predetermined period of time of the retriggerable monostable multivibrator 682 acting in response to the onset of the first peak has not yet elapsed, then the predetermined period of time will be restarted amidst the currently occurring predetermined period of time in response to the onset of the second peak. As a result, the amount of time during which the retriggerable monostable multivibrator causes the analog switch 681 to break the coupling of the talk-through microphone 185 to the audio amplifier 688 is extendable so as to avoid allowing either a first peak or subsequent peaks to be conveyed to the input of the audio amplifier 688. Although embodiments are possible in which the retriggerable monostable multivibrator 682 is replaced with some other form of timing device that is not retriggerable, it is preferred that a retriggerable form of timing device be used. Returning to the infantryman scenario, having a retriggerable form of timing device will allow the pulsed attenuator 680 to better accommodate the infantryman firing a "machine gun" or other fully automatic weapon that fires a stream of bullets in rapid succession such that there is a rapid succession of gunshot sounds, and thus, a rapid succession of sounds that each begin with such an initial peak of undesirably high amplitude. With the detection of the onset of each such peak, the retriggerable monostable multivibrator 682 is retriggered to repeatedly extend the period of time during which the retriggerable monostable multivibrator 682 causes the analog switch 681 (through the MOSFET) to remain open so as to prevent all of such peaks in the rapid succession of gunshot sounds from being conveyed to the input of the audio amplifier 688.

FIG. 3 depicts portions of another possible variant of the electrical architecture 2000*a* introduced in FIGS. 2*a* and 2*b*. This variant differs from the variant depicted in FIGS. 2*a* and 2*b* to the extent that talk-through functionality is combined with ANR functionality. Again, for sake of clarity, components of the audio circuit 600 associated with only one of the earpieces 110 (and therefore, only one of the acoustic drivers 115) are depicted. Given the extensive treatment of numerous implementation details just provided with regard to FIGS. 2*a* and 2*b*, such details are not repeated in FIG. 3, and therefore, FIG. 3 presents a somewhat higher-level depiction.

As already depicted and discussed with regard to FIG. 2*b*, the audio circuit 600 incorporates the differential amplifier 625, pulsed attenuator 680, talk-through circuit 685 and envelope detector 626. However, as also depicted, and differing from what has been depicted and discussed with regard to FIG. 2*b*, the audio circuit 600 further incorporates a summing node 615, a pulsed attenuator 690 and an ANR circuit 695. The pulsed attenuator 690 is coupled by its input to one of the feedforward microphones 195, and is coupled by its output to the ANR circuit 695. In turn, the ANR circuit 695, like the talk-through circuit 685, is coupled to the envelope detector 626 to receive the results of integrating an amplified form of signals representing sounds detected by the communications microphone 125. Further, the summing node 615 is interposed between the acoustic driver 115 and the outputs of the talk-through circuit 685 and the ANR circuit 695 to combine these outputs into a single signal with which the acoustic driver 115 is driven.

As those familiar with ANR will readily recognize, both feedback-based and feedforward-based forms of ANR entail detecting unwanted noise sounds with one or more microphones, deriving anti-noise sounds and then acoustically outputting those anti-noise sounds at a location and with a timing selected to cause destructive acoustic interference with the unwanted noise sounds to at least reduce their acoustic amplitude. In embodiments in which the headset 1000*a* incorporates feedforward-based ANR, at least one of the feedforward microphones 195 is carried by a portion of the headset 1000*a* such that it is acoustically coupled to the environment external to the acoustic volumes enclosed by the earpieces 110 in the vicinity of an ear in order to detect unwanted noise sounds in that external environment. The ANR circuit 695 receives electrical signals representing the detected noise sounds, and employs those noise sounds as reference sounds from which to generate the anti-noise sounds provided to the acoustic driver 115 (through the summing node 615).

In a manner not unlike the previously discussed compression of signals received from the talk-through microphone 185 within the talk-through circuit 685 under the control of the envelope detector 626, the ANR circuit 695 similarly compresses signals received from the feedforward microphone 195 under the control of the envelope detector 626. Reducing the gain of the signal representing noise sounds detected by the feedforward microphone 195 in response to a user of the headset 1000*a* speaking may be deemed desirable, just as in the case of talk-through functionality, to avoid the conveyance of the user's own speech sounds to the user's own ears with an unnaturally high amplitude and/or with other unnaturally altered characteristics. Although it is commonplace for much of the range of frequencies of sound in which ANR is employed to be largely below the range of frequencies of sound normally associated with human speech, there is some degree of overlap between these two ranges. As a result, the speech sounds of a user of the communications headset 1000 (especially a user with a deeper voice) that are detected by the feedforward microphone 195 may be treated by the ANR circuit 695 as unwanted environmental noise sounds for which it generates anti-noise sounds that are caused to be acoustically output by the acoustic driver 115. This acoustic output of anti-noise sounds meant to reduce lower frequency portions of their speech may produce undesirable acoustic artifacts that the user may find unpleasant or distracting. Reducing the gain of the signal representing noise sounds detected by the feedforward ANR microphone 195 as the user speaks preserves at least some degree of ANR functionality, while also reducing at least the amplitude of such speech-based anti-noise sounds.

Like the talk-through circuit 685 being coupled to the talk-through microphone 185 through the pulsed attenuator 680, the ANR circuit 695 is coupled to the feedforward microphone 195 through the pulsed attenuator 690. The pulsed attenuator 690 is preferably substantially identical to the pulsed attenuator 680, and performs very much the same function. Although the ANR circuit 695 would attempt to employ a noise sound detected by the feedforward microphone 195 that includes a single undesirably high peak in amplitude to create an anti-noise sound, in so doing, the ANR circuit 695 may create a distorted anti-noise sound having its own undesirably high peak in amplitude in a failed attempt to counter the original noise sound. As those familiar with feedforward-based ANR will readily recognize, with sounds of sufficiently high amplitude, it is likely that the feedforward microphone 195 ceases to behave linearly, and thus, the attempt to create an anti-noise sound with such a high peak in amplitude is likely to actually create more noise. Further, not unlike the closed-loop compressor within the talk-through circuit 685, it is believed likely that a corresponding compressor within the ANR circuit 695 would likely be unable to act quickly enough to prevent this from occurring. Hence the inclusion of the corresponding pulsed attenuator 690.

It should be noted that although the talk-through microphone 185 and the feedforward ANR microphone 195 are depicted as being separate and distinct microphones, alternate embodiments are possible in which a shared microphone replaces both to provide a common sound detection input for both functions. This may be possible due to both the talk-through microphone 185 and the feedforward ANR microphone 195 being acoustically coupled to the external environment, and due to both preferably not being noise-canceling type microphones such that they are both indeed able to detect far-field sounds along with near-field sounds (unlike the communications microphone 125, which as previously discussed, is a noise-canceling type of microphone structured to detect near-field sounds while largely ignoring far-field sounds). This depends, at least partially, on whether one or more locations exist on the structure of the communications headset at which a single microphone may be positioned (so as to be acoustically coupled to the external environment surrounding the headset 1000*a* and its user's head) that will allow detection of external sounds in a manner that will be effective for both functions. It should be further noted that were a single such microphone to be used, then it may be that only a single pulsed attenuator need interposed between that single microphone and both the talk-through circuit 685 and the ANR circuit 695.

Again, it should be noted that only a single acoustic driver 115 and its associated circuitry within the audio circuit 600 (e.g., the talk-through circuit 685 and the ANR circuit 695) are depicted for sake of visual clarity. Thus, in embodiments of the communications headset 1000 having a pair of the earpieces 110, there would be a pair of the acoustic drivers 115, each having an associated one of a pair of the talk-through circuits 685 and an associated one of a pair of ANR circuits 695 coupled to it, and the single envelope detector

626 would be coupled to each of those talk-through circuits 685 and each one of those ANR circuits 695.

Figure 4A:
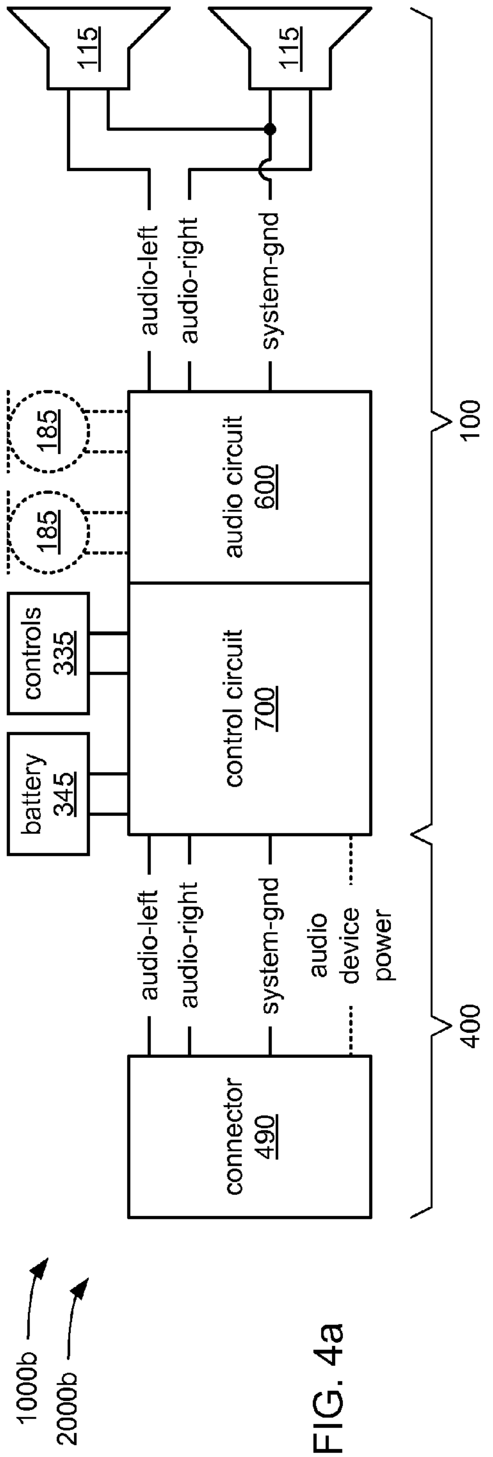
FIGS. 4*a* and 4*b* are block diagrams of portions of a possible electrical architecture of the headset of FIG. 1*b*.
Figure 4B:
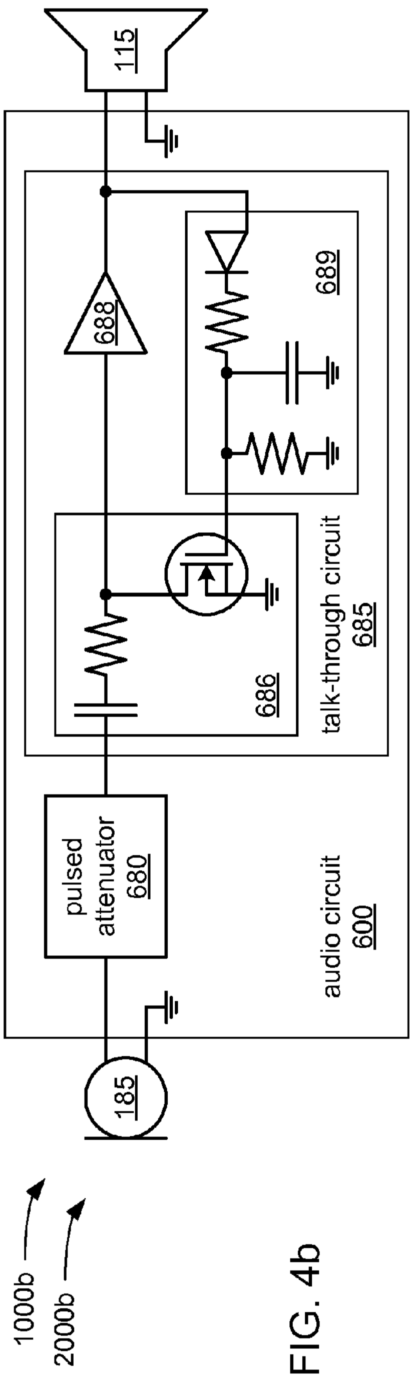

FIGS. 4*a* and 4*b* provide depictions of an electrical architecture 2000*b* that may be employed by the headset 1000*b* of FIG. 1*b*, and of a variant of the audio circuit 600 that may be employed within the electrical architecture 2000*b*. What is depicted and the manner of its depiction in each of FIGS. 4*a* and 4*b* are meant to be substantially analogous to FIGS. 2*a* and 2*b*, respectively. Indeed, as depicted, the electrical architecture 2000*b* is substantially similar to the electrical architecture 2000*a*, and in particular, many aspects of the audio circuit 600 in both architectures are substantially similar and function in substantially similar ways. However, a substantial difference of the electrical architecture 2000*b* from the electrical architecture 2000*a* is the lack of a communications microphone and other supporting components for implementing two-way communications in the electrical architecture 2000*b*, reflecting the fact that the headset 2000*a* supports two-way audio communications, whereas the headset 2000*b* does not. Another substantial difference is that the control circuit 700 and the audio circuit 600 are co-located within the head assembly 100 in the headset 1000*b*, thus eliminating the separate control box 300 and upper cable 200 of the headset 1000*a* in the headset 1000*b*.

Thus, the mic-lo and mic-high conductors depicted as part of the electrical architecture 2000*a* in FIGS. 2*a-b*, do not exist in the electrical architecture 2000*b*, and are therefore not depicted in FIGS. 4*a-b*. The pulsed attenuator 680 is depicted simply as a box in FIG. 4*b* as it would likely be implemented substantially similarly to what was described with regard to FIG. 2*b*. In contrast, the talk-through circuit 685 is depicted in more detail in FIG. 4*b* to clearly depict is lack of the voltage-controlled attenuator 687 versus the variant of talk-through circuit 685 depicted in FIG. 2*b*.

Other embodiments and implementations are within the scope of the following claims and other claims to which the applicant may be entitled.

What is claimed is:

1. A method of controlling sounds acoustically output by an acoustic driver disposed within a casing of an earpiece of a headset, the method comprising:

monitoring a signal representing sounds detected by a microphone of the headset that is acoustically coupled to the environment external to the casing;

detecting an onset of a peak in the signal that exceeds a predetermined voltage level and that has a rate of change in voltage level that exceeds a predetermined rate of change; and operating a switch to disconnect the signal from an input of an amplifier, thereby preventing the peak from being conveyed to the amplifier.

2. The method of claim 1, further comprising operating the switch to reconnect the signal after a predetermined period of time.

3. The method of claim 2, wherein the predetermined period of time is retriggerable.

4. The method of claim 3, wherein the predetermined period of time is selected to compress a peak associated with a sound of a gunshot.

5. The method of claim 1, wherein at least one of the predetermined voltage level and the predetermined rate of change is selected to compress a peak associated with a sound of a gunshot.

6. A headset comprising:

a first earpiece comprising:

a first casing; and a first acoustic driver disposed therein;

a first microphone carried by structure of the headset and acoustically coupled to an environment external to the first casing; and an audio circuit coupled to the first acoustic driver and the first microphone, the audio circuit receiving a signal representing sounds detected by the first microphone and providing an output to the first acoustic driver, the audio circuit comprising a switch and an amplifier;

wherein the audio circuit is configured to operate the switch to disconnect the signal from the amplifier in response to detecting an onset of a peak in the signal that exceeds a predetermined voltage level and that has a rate of change in voltage level that exceeds a predetermined rate of change, thereby preventing the peak from being conveyed to the amplifier.

7. The headset of claim 6, wherein the audio circuit is further configured to operate the switch to reconnect the signal after a predetermined period of time.

8. The headset of claim 7, further comprising a retriggerable monostable multivibrator set for the predetermined period of time, configured to operate the switch to reconnect the signal after the predetermined period of time, and able to be retriggered to restart the predetermined period time amidst the predetermined period of time.

9. The headset of claim 7, wherein the predetermined period of time is selected to compress a peak associated with a sound of a gunshot.

10. The headset of claim 6, wherein at least one of the predetermined voltage level and the predetermined rate of change is selected to compress a peak associated with a sound of a gunshot.

11. The headset of claim 6, wherein the first microphone is a talk-through microphone and the audio circuit comprises a talk-through circuit.

12. The headset of claim 6, further comprising:

a second earpiece comprising:

a second casing; and a second acoustic driver disposed therein;

a second microphone carried by structure of the communications headset and acoustically coupled to an environment external to the second casing;

wherein the audio circuit is coupled to the second acoustic driver and the second microphone, and comprises a second switch, the audio circuit receiving another signal representing sounds detected by the second microphone and providing an output to the second acoustic driver;

wherein the audio circuit operates the second switch to disconnect the other signal in response to detecting an onset of a peak in the other signal that exceeds the predetermined voltage level and that has a rate of change in voltage level that exceeds the predetermined rate of change.

13. A method of controlling sounds acoustically output by an acoustic driver disposed within a casing of an earpiece of a headset, the method comprising:

monitoring a signal representing sounds detected by a microphone of the headset that is acoustically coupled to the environment external to the casing;

detecting an onset of a peak in the signal that exceeds a predetermined voltage level and that has a rate of change in voltage level that exceeds a predetermined rate of change; and compressing the signal for a predetermined period of time, thereby preventing the peak from being conveyed to an input of an amplifier.

14. The method of claim 13, wherein the predetermined period of time is retriggerable.

15. The method of claim 13, wherein the predetermined period of time is selected to compress a peak associated with a sound of a gunshot.

16. The method of claim 14, wherein at least one of the predetermined voltage level and the predetermined rate of change is selected to compress a peak associated with a sound of a gunshot.

17. A headset comprising:

a first earpiece comprising:

a first casing; and a first acoustic driver disposed therein;

a first microphone carried by structure of the communications headset and acoustically coupled to an environment external to the first casing; and an audio circuit coupled to the first acoustic driver and the first microphone, the audio circuit receiving a signal representing sounds detected by the first microphone and providing an output to the first acoustic driver, the audio circuit comprising a switch and an amplifier;

wherein the audio circuit is configured to compress the signal for a predetermined period of time in response to detecting an onset of a peak in the signal that exceeds a predetermined voltage level and that has a rate of change in voltage level that exceeds a predetermined rate of change, thereby preventing the peak from being conveyed to the amplifier.

18. The headset of claim 17, further comprising a retriggerable monostable multivibrator set for the predetermined period of time, configured to cause the signal to be compressed for the predetermined period of time, and able to be retriggered to restart the predetermined period time amidst the predetermined period of time.

19. The headset of claim 17, wherein the predetermined period of time is selected to compress a peak associated with a sound of a gunshot.

20. The headset of claim 17, wherein at least one of the predetermined voltage level and the predetermined rate of change is selected to compress a peak associated with a sound of a gunshot.

21. The headset of claim 17, wherein the first microphone is a talk-through microphone and the audio circuit comprises a talk-through circuit.

22. The headset of claim 17, further comprising:

a second earpiece comprising:

a second casing; and a second acoustic driver disposed therein;

a second microphone carried by structure of the communications headset and acoustically coupled to an environment external to the second casing;

wherein the audio circuit is coupled to the second acoustic driver and the second microphone, the audio circuit receiving another signal representing sounds detected by the second microphone and providing an output to the second acoustic driver; and wherein the audio circuit is configured to compress the other signal in response to detecting an onset of a peak in the other signal that exceeds the predetermined voltage level and that has a rate of change in voltage level that exceeds the predetermined rate of change.

* * * * *